US 7,236,819 B2

(12) United States Patent
Brockway et al.

(10) Patent No.: US 7,236,819 B2
(45) Date of Patent: Jun. 26, 2007

(54) SEPARATION OF A SUBCUTANEOUS CARDIAC SIGNAL FROM A PLURALITY OF COMPOSITE SIGNALS

(75) Inventors: Marina Brockway, Shoreview, MN (US); Carlos Alberto Ricci, Apple Valley, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 388 days.

(21) Appl. No.: 10/741,814

(22) Filed: Dec. 19, 2003

(65) Prior Publication Data

US 2004/0230128 A1 Nov. 18, 2004

Related U.S. Application Data

(60) Provisional application No. 60/462,272, filed on Apr. 11, 2003.

(51) Int. Cl.
*A61B 5/04* (2006.01)
(52) U.S. Cl. .............. 600/509; 600/511; 600/517; 600/518; 607/5
(58) Field of Classification Search ............ 600/510, 600/518, 511, 517; 607/5
See application file for complete search history.

(56) References Cited

U.S. PATENT DOCUMENTS

| | | | |
|---|---|---|---|
| 4,562,841 A | 1/1986 | Brockway et al. |
| 4,953,551 A | 9/1990 | Mehra et al. |
| 5,036,849 A | 8/1991 | Hauck et al. |
| 5,133,353 A | 7/1992 | Hauser |
| 5,170,784 A | 12/1992 | Ramon et al. |
| 5,179,945 A | 1/1993 | Van Hofwegen et al. |
| 5,203,348 A | 4/1993 | Dahl et al. |
| 5,209,229 A | 5/1993 | Gilli |

(Continued)

FOREIGN PATENT DOCUMENTS

WO 1992/17240 10/1992

(Continued)

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner*—Robert Pezzuto
*Assistant Examiner*—Shevon Johnson
(74) *Attorney, Agent, or Firm*—Hollingsworth & Funk, LLC

(57) ABSTRACT

A cardiac monitoring and/or stimulation method and systems provide monitoring, defibrillation and/or pacing therapies, including systems detecting and/or treating cardiac arrhythmia. A system includes a housing coupled to a plurality of electrodes configured for subcutaneous non-intrathoracic sensing. A signal processor receives a plurality of composite signals associated with a plurality of sources, separates a signal from the plurality of composite signals using blind source separation, and identifies a cardiac signal. The signal processor may iteratively separate signals from the plurality of composite signals until the cardiac signal is identified. A method of signal separation includes detecting a plurality of composite signals at a plurality of locations, separating a signal using blind source separation, and identifying a cardiac signal. The separation may include a principal component analysis and/or an independent component analysis. The composite signals may be filtered before separation using band-pass filtering, adaptive, or other filters.

61 Claims, 10 Drawing Sheets

U.S. PATENT DOCUMENTS

| | | |
|---|---|---|
| 5,230,337 A | 7/1993 | Dahl et al. |
| 5,261,400 A | 11/1993 | Bardy |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,331,966 A | 7/1994 | Bennett et al. |
| 5,334,222 A | 8/1994 | Salo et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,439,482 A | 8/1995 | Adams et al. |
| 5,441,518 A | 8/1995 | Adams et al. |
| 5,468,254 A | 11/1995 | Hahn et al. |
| 5,531,779 A | 7/1996 | Dahl et al. |
| 5,540,727 A | 7/1996 | Tockman et al. |
| 5,545,186 A | 8/1996 | Olson et al. |
| 5,545,202 A | 8/1996 | Dahl et al. |
| 5,603,732 A | 2/1997 | Dahl et al. |
| 5,620,466 A | 4/1997 | Haefner et al. |
| 5,634,938 A | 6/1997 | Swanson et al. |
| 5,641,326 A | 6/1997 | Adams |
| 5,662,688 A | 9/1997 | Haefner et al. |
| 5,697,953 A | 12/1997 | Kroll et al. |
| 5,704,365 A | 1/1998 | Albrecht et al. |
| 5,724,984 A | 3/1998 | Arnold et al. |
| 5,827,326 A | 10/1998 | Kroll et al. |
| 5,836,987 A | 11/1998 | Baumann et al. |
| 5,855,593 A | 1/1999 | Olson et al. |
| 5,895,414 A | 4/1999 | Sanchez-Zambrano |
| 5,916,243 A | 6/1999 | KenKnight et al. |
| 5,957,956 A | 9/1999 | Kroll et al. |
| 6,026,320 A | 2/2000 | Carlson et al. |
| 6,044,298 A | 3/2000 | Salo et al. |
| 6,055,454 A | 4/2000 | Heemels |
| 6,115,628 A | 9/2000 | Stadler et al. |
| 6,141,581 A | 10/2000 | Olson et al. |
| 6,148,230 A | 11/2000 | KenKnight |
| 6,221,011 B1 | 4/2001 | Bardy |
| 6,227,072 B1 | 5/2001 | Ritchey et al. |
| 6,259,947 B1 | 7/2001 | Olson et al. |
| 6,270,457 B1 | 8/2001 | Bardy |
| 6,280,380 B1 | 8/2001 | Bardy |
| 6,280,462 B1 | 8/2001 | Hauser et al. |
| 6,285,907 B1 | 9/2001 | Kramer et al. |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,371,922 B1 | 4/2002 | Baumann et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,424,865 B1 | 7/2002 | Ding |
| 6,438,410 B2 | 8/2002 | Hsu et al. |
| 6,440,066 B1 | 8/2002 | Bardy |
| 6,459,929 B1 | 10/2002 | Hopper et al. |
| 6,480,733 B1 | 11/2002 | Turcott |
| 6,487,443 B2 | 11/2002 | Olson et al. |
| 6,491,639 B1 | 12/2002 | Turcott |
| 6,496,715 B1 | 12/2002 | Lee et al. |
| 6,505,067 B1 | 1/2003 | Lee et al. |
| 6,512,940 B1 | 1/2003 | Brabec et al. |
| 6,522,915 B1 | 2/2003 | Ceballos et al. |
| 6,542,775 B2 | 4/2003 | Ding et al. |
| 6,564,106 B2 | 5/2003 | Guck et al. |
| 6,597,951 B2 | 7/2003 | Kramer et al. |
| 6,607,509 B2 | 8/2003 | Bobroff et al. |
| 6,615,083 B2 | 9/2003 | Kupper |
| 6,622,046 B2 | 9/2003 | Fraley et al. |
| 6,701,170 B2 * | 3/2004 | Stetson ............ 600/323 |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0085741 A1 | 7/2002 | Shimizu |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissman et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0136328 A1 | 9/2002 | Shimizu |
| 2003/0004546 A1 | 1/2003 | Casey |
| 2003/0004552 A1 | 1/2003 | Plombon et al. |
| 2003/0023175 A1 | 1/2003 | Arzbaecher et al. |
| 2003/0036778 A1 | 2/2003 | Ostroff et al. |
| 2003/0045904 A1 | 3/2003 | Bardy et al. |
| 2003/0069609 A1 | 4/2003 | Thompson |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0204146 A1 | 10/2003 | Carlson |
| 2003/0212436 A1 | 11/2003 | Brown |
| 2004/0111021 A1 | 6/2004 | Olson |
| 2004/0260522 A1 * | 12/2004 | Albera et al. ............ 702/189 |
| 2005/0010120 A1 * | 1/2005 | Jung et al. ............ 600/509 |

FOREIGN PATENT DOCUMENTS

| | | |
|---|---|---|
| WO | WO 92/20402 | 11/1992 |
| WO | WO 03/003905 | 1/2003 |

OTHER PUBLICATIONS

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stilmuli*, IEEE Trans On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits and Marek Malik, *Defibrillation Threshold (DFT) Model of a Fully Subcutaneous ICD System*, Europace Supplements, vol. 2, Jun. 2001 at column 778, p. 883.

Stirbis et al., *Optmizing the Shape of Implanted Artificial Pacemakers* Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

A. Hyvännen and E. Oja, *Independent Component Analysis: A Tutorial*, Helsinski Univ. Technology, Apr. 1999.

Pierre Comon, *Independent component analysis, A new concept?*, Signal Processing, vol. 36, No. 3, pp. 287-314 (Apr. 1994).

Adel Belouchrani and Moeness G. Amin, *Blind Source Separation Based on Time-Frequency Signal Representations*, IEEE Transactions on Signal Processing, vol. 46, No. 11, pp. 2888-2897 (Nov. 1998).

Vicente Zarzoso and Asoke K. Nandi, *Blind Separation of Independent Sources for Virtually Any Source Probability Density Function*, IEEE Transactions on Signal Process, vol. 47, No. 9, pp. 2419-2432 (Sep. 1999).

Vicente Zarzoso and Asoke K. Nandi, *Noninvasive Fetal Electrocardiogram Extraction: Blind Separation Versus Adaptive Noise Cancellation*, IEEE Transactions on Biomedical Engineering, vol. 48, No. 1, pp. 12-18 (Jan. 2001).

Philippe Gallois, et al., *Multi-Channel Analysis of the EEG Signals and Statistic Particularities for Epileptic Seizure Forecast*, Second Joint EMBS/BMES Conference, pp. 208-215 (OCt. 23-26, 2002).

J.J. Rieta, et al., *Atrial Activity Extraction Based on Blind Source Separation as an Alternative to QRST Cancellation for Atrial Fibrillation Analysis*, Computers in Cardiology, vol. 27, pp. 69-72 (2000).

Krahn, A.D. et al. *Recurrent syncope. Experience with an implantable loop record*. Cardiol. Clin., vol. 15(2), May 1997, pp. 316-326 (Abstract only).

* cited by examiner

SEPARATION OF A SUBCUTANEOUS CARDIAC SIGNAL FROM A PLURALITY OF COMPOSITE SIGNALS

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to implantable medical devices and, more particularly, to subcutaneous cardiac sensing and/or stimulation devices employing cardiac signal separation.

BACKGROUND OF THE INVENTION

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60–100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and can be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria can also adversely affect the ventricular rate.

Ventricular tachycardia occurs, for example, when electrical activity arises in the ventricular myocardium at a rate more rapid than the normal sinus rhythm. Ventricular tachycardia can quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical implantable cardioverter/defibrillators (ICDs) include one or more endocardial leads to which at least one defibrillation electrode is connected. Such ICDs are capable of delivering high-energy shocks to the heart, interrupting the ventricular tachyarrhythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. Primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure. Subcutaneous ICDs are being developed to address these issues.

There is a need for improved electrode configurations specific to the needs of subcutaneous electrode placement and to address the noise associated with subcutaneous electrode placement. There is a further need for a method of improving the signal to noise ratio of the cardiac signal in subcutaneous ICDs. The present invention fulfills these and other needs, and addresses deficiencies in known systems and techniques.

SUMMARY OF THE INVENTION

The present invention is directed to cardiac monitoring and/or stimulation methods and systems that, in general, provide transthoracic monitoring, defibrillation therapies, pacing therapies, or a combination of these capabilities. Embodiments of the present invention include those directed to subcutaneous cardiac monitoring and/or stimulation methods and systems that detect and/or treat cardiac activity or arrhythmias.

According to one embodiment of the invention, a medical system includes a housing having a medical device disposed within the housing. The housing is coupled to a plurality of electrodes configured for subcutaneous non-intrathoracic sensing. A signal processor is coupled to the plurality of electrodes and configured to receive a plurality of composite signals associated with a plurality of sources sensed by at least some of the electrodes. The signal processor is further configured to separate a signal from the plurality of composite signals and identify the separated signal as a cardiac signal.

In another embodiment of the present invention, the signal processor iteratively separates signals from the plurality of composite signals until the cardiac signal is identified. The processor may include a filter configured to filter the plurality of composite signals prior to separating the signal.

In another aspect of the present invention, a method of signal separation includes detecting a plurality of composite signals at a plurality of subcutaneous non-intrathoracic locations, the plurality of composite signals associated with a plurality of sources. A signal is separated, using blind source separation, from the plurality of composite signals, and identified as a cardiac signal. The method may further include a principal component analysis and/or an independent component analysis to perform the blind source separation. The composite signals may be filtered before separation using band-pass filtering, adaptive, or other filters.

In another embodiment of the present invention, an estimate of the spatial covariance matrix for a composite signal matrix is formed from the plurality of composite signals. Independent component analysis and principal component analysis may be performed using the estimate of the spatial covariance matrix, producing a set of eigenvalues and associated eigenvectors. An eigenvector associated with a largest magnitude eigenvalue may be used to separate the cardiac signal from the plurality of composite signals by multiplying the composite signal matrix by the eigenvector.

The signal may be separated iteratively from the plurality of composite signals using an eigenvector associated with a next-largest magnitude eigenvalue for each iteration, until the cardiac signal is identified. The cardiac signal may be identified using a local peak density (LPD) of the separated signal, wherein the LPD is within a predetermined range. The cardiac signal may also be identified using beat detection on the separated signal, wherein a beat rate is within a predetermined range, or by using a local rate of occurrence of significant points in the separated signal, wherein the local rate of occurrence is within a predetermined range. The cardiac signal may also be identified using a morphology of the separated signal, wherein the morphology satisfies a physiological characteristic.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
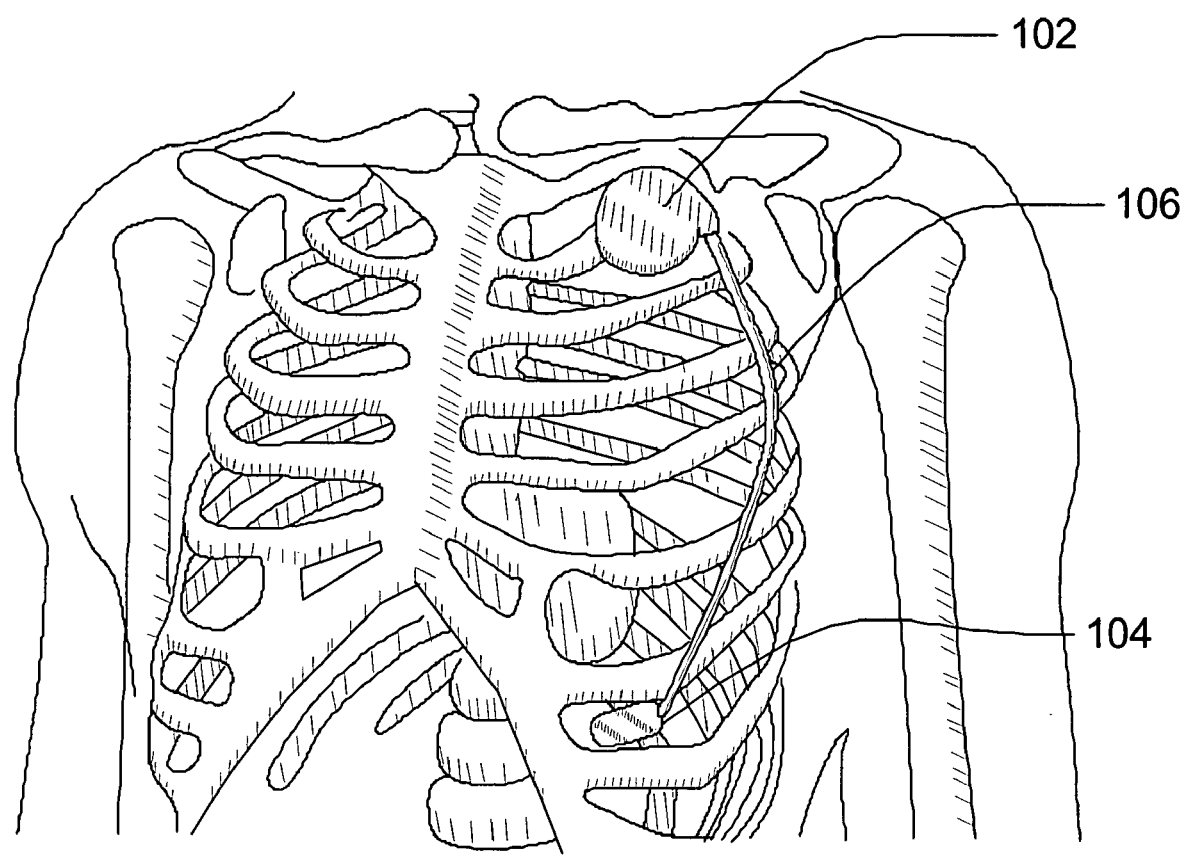
FIGS. 1A and 1B are views of a transthoracic cardiac sensing and/or stimulation device as implanted in a patient in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

In general terms, an implantable noise canceling lead system may be used with a subcutaneous cardiac monitoring and/or stimulation device. One such device is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more noise canceling leads incorporating electrodes may be located in direct contact with the heart, great vessel or coronary vasculature, such as via one or more leads implanted by use of conventional transvenous delivery approaches. In a further implementation, for example, one or more subcutaneous noise canceling electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart. Examples of noise canceling subcutaneous electrodes and electrode arrays are described in commonly owned US Publication No. 2004/0230243, which is hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Exemplary ICD circuitry, structures and functionality, aspects of which may be incorporated in an ITCS device of a type that may benefit from noise canceling electrode configurations, are disclosed in commonly owned U.S. Pat. Nos. 5,133,353; 5,179,945; 5,314,459; 5,318,597; 5,620,466; and 5,662,688, which are hereby incorporated herein by reference in their respective entireties.

In particular configurations, systems and methods may perform functions traditionally performed by pacemakers, such as providing various pacing therapies as are known in the art, in addition to cardioversion/defibrillation therapies. Exemplary pacemaker circuitry, structures and functionality, aspects of which may be incorporated in an ITCS device of a type that may benefit from signal separation, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference in their respective entireties. It is understood that ITCS device configurations may provide for non-physiologic pacing support in addition to, or to the exclusion of, bradycardia and/or anti-tachycardia pacing therapies.

An ITCS device in accordance with the present invention may implement diagnostic and/or monitoring functions as well as provide cardiac stimulation therapy. Exemplary cardiac monitoring circuitry, structures and functionality, aspects of which may be incorporated in an ITCS device of a type that may benefit from noise canceling electrode configurations, are disclosed in commonly owned U.S. Pat. Nos. 5,313,953; 5,388,578; and 5,411,031, which are hereby incorporated herein by reference in their respective entireties.

An ITCS device may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the instant disclosure may be implemented in a wide range of implantable medical devices, and that such embodiments and features are not limited to the particular devices described herein.

Figure 1B:
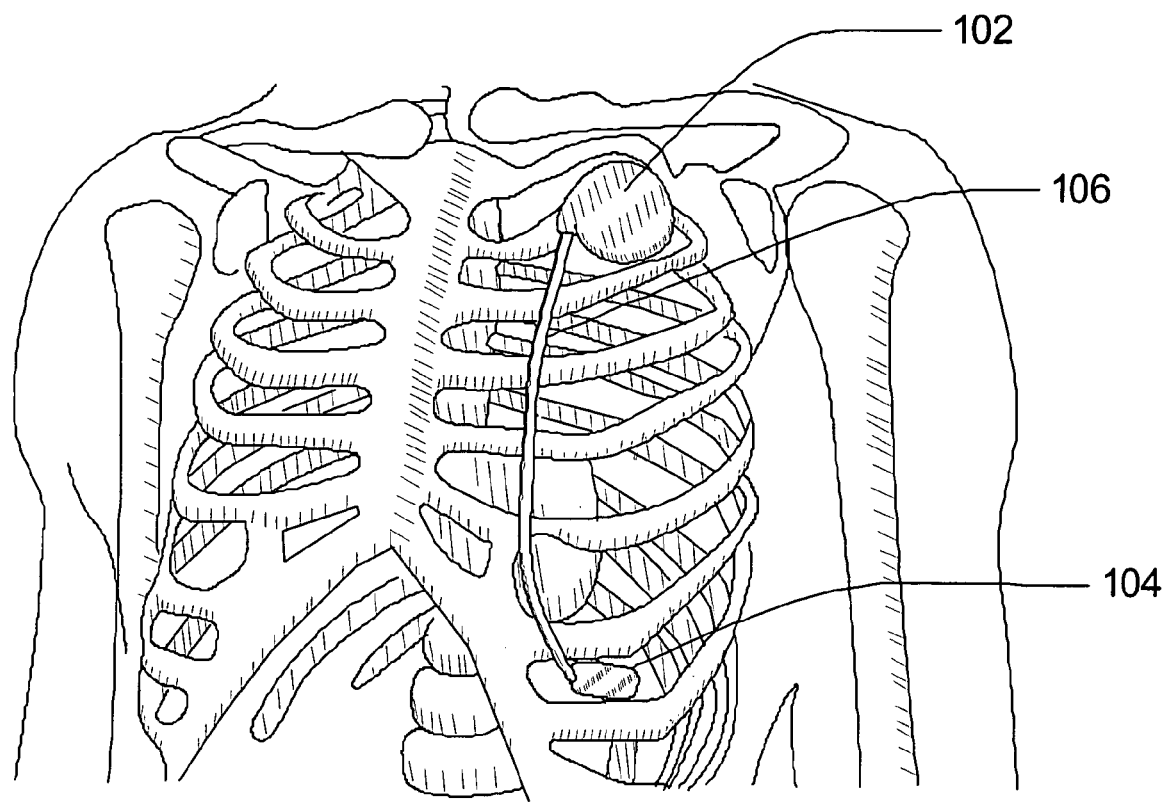

Referring now to FIGS. 1A and 1B of the drawings, there is shown a configuration of a transthoracic cardiac sensing and/or stimulation (ITCS) device having components implanted in the chest region of a patient at different locations. In the particular configuration shown in FIGS. 1A and 1B, the ITCS device includes a housing 102 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Communications circuitry is disposed within the housing 102 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 1A and 1B, a subcutaneous electrode 104 may be positioned under the skin in the chest region and situated distal from the housing 102. The subcutaneous and, if applicable, housing electrode(s) may be positioned about the heart at various locations and orientations, such as at various anterior and/or posterior locations relative to the heart. The subcutaneous electrode 104 is coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

In one configuration, the lead assembly 106 is generally flexible and has a construction similar to conventional implantable, medical electrical leads (e.g., defibrillation leads or combined defibrillation/pacing leads). In another configuration, the lead assembly 106 is constructed to be somewhat flexible, yet has an elastic, spring, or mechanical memory that retains a desired configuration after being shaped or manipulated by a clinician. For example, the lead assembly 106 may incorporate a gooseneck or braid system that may be distorted under manual force to take on a desired shape. In this manner, the lead assembly 106 may be shape-fit to accommodate the unique anatomical configuration of a given patient, and generally retains a customized shape after implantation. Shaping of the lead assembly 106 according to this configuration may occur prior to, and during, ITCS device implantation.

In accordance with a further configuration, the lead assembly 106 includes a rigid electrode support assembly, such as a rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure may be formed from a structural plastic, composite, or metallic material, and comprises, or is covered by, a biocompatible material. Appropriate electrical isolation between the housing 102 and subcutaneous electrode 104 is provided in cases where the elongated structure is formed from an electrically conductive material, such as metal.

In one configuration, the rigid electrode support assembly and the housing 102 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the rigid electrode support assembly and housing 102. The header block arrangement may be provided on the housing 102 or the rigid electrode support assembly. Alternatively, a mechanical/electrical coupler may be used to establish mechanical and electrical connections between the rigid electrode support assembly and housing 102. In such a configuration, a variety of different electrode support assemblies of varying shapes, sizes, and electrode configurations may be made available for physically and electrically connecting to a standard ITCS device housing 102.

It is noted that the electrodes and the lead assembly 106 may be configured to assume a variety of shapes. For example, the lead assembly 106 may have a wedge, chevron, flattened oval, or a ribbon shape, and the subcutaneous electrode 104 may comprise a number of spaced electrodes, such as an array or band of electrodes. Moreover, two or more subcutaneous electrodes 104 may be mounted to multiple electrode support assemblies 106 to achieve a desired spaced relationship amongst subcutaneous electrodes 104.

An ITCS device may incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference in their respective entireties.

Figure 1C:
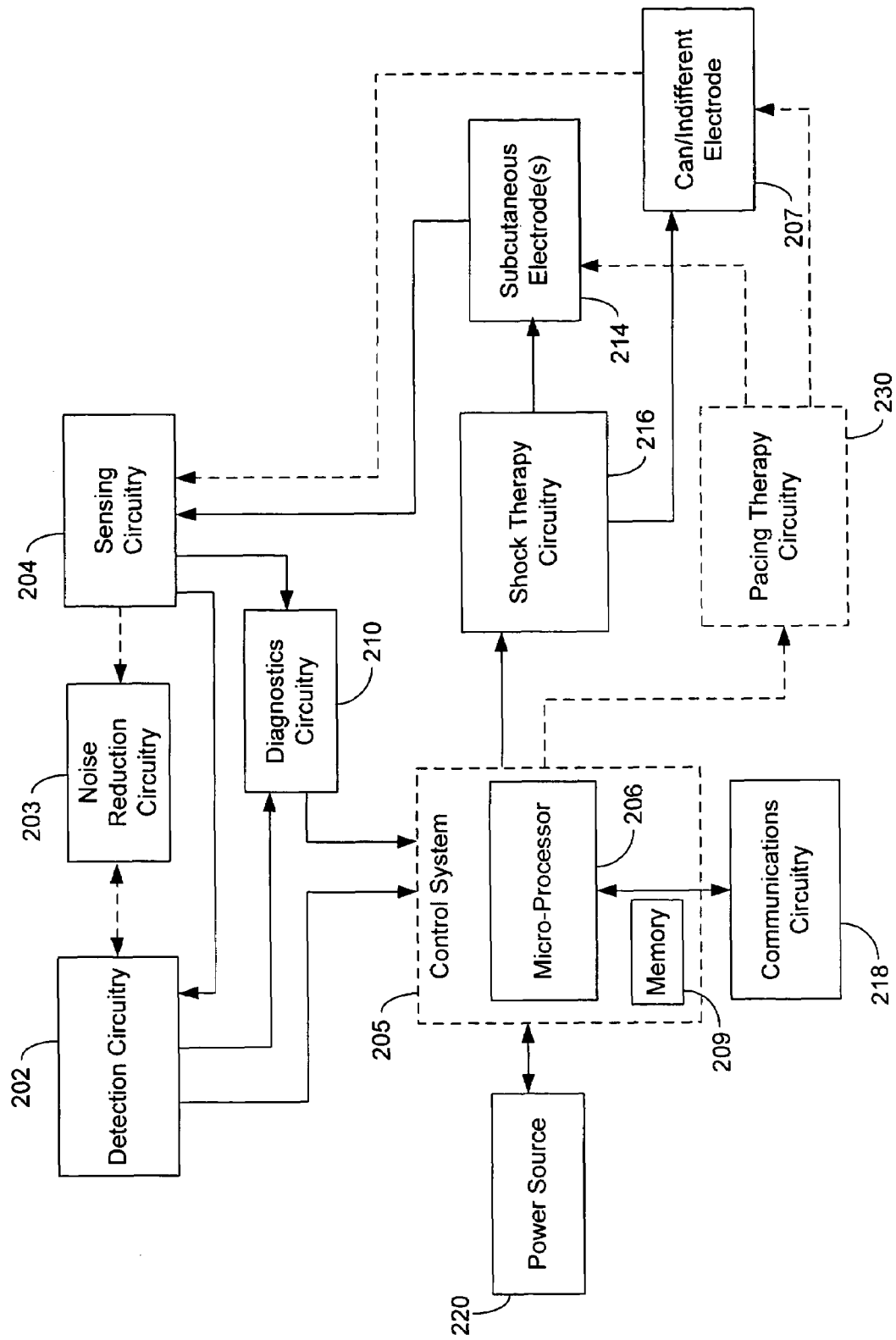
FIG. 1C is a block diagram illustrating various components of a transthoracic cardiac sensing and/or stimulation device in accordance with an embodiment of the present invention.

FIG. 1C is a block diagram depicting various components of an ITCS device in accordance with one configuration. According to this configuration, the ITCS device incorporates a processor-based control system 205 which includes a micro-processor 206 coupled to appropriate memory (volatile and non-volatile) 209, it being understood that any logic-based control architecture may be used. The control system 205 is coupled to circuitry and components to sense, detect, and analyze electrical signals produced by the heart and deliver electrical stimulation energy to the heart under predetermined conditions to treat cardiac arrhythmias. In certain configurations, the control system 205 and associated components also provide pacing therapy to the heart. The electrical energy delivered by the ITCS device may be in the form of low energy pacing pulses or high-energy pulses for cardioversion or defibrillation.

Cardiac signals are sensed using the subcutaneous electrode(s) 214 and the can or indifferent electrode 207 provided on the ITCS device housing. Cardiac signals may also be sensed using only the subcutaneous electrodes 214, such as in a non-active can configuration. As such, unipolar, bipolar, or combined unipolar/bipolar electrode configurations as well as multi-element noise canceling electrodes and combinations of noise canceling and standard electrodes may be employed. The sensed cardiac signals are received by sensing circuitry 204, which includes sense amplification circuitry and may also include filtering circuitry and an analog-to-digital (A/D) converter. The sensed cardiac signals processed by the sensing circuitry 204 may be received by noise reduction circuitry 203, which may further reduce noise before signals are sent to the detection circuitry 202.

Noise reduction circuitry 203 may also be incorporated after sensing circuitry 204 in cases where high power or computationally intensive noise reduction algorithms are required. The noise reduction circuitry 203, by way of amplifiers used to perform operations with the electrode signals, may also perform the function of the sensing circuitry 204. Combining the functions of sensing circuitry 204 and noise reduction circuitry 203 may be useful to minimize the necessary componentry and lower the power requirements of the system.

In the illustrative configuration shown in FIG. 1C, the detection circuitry 202 is coupled to, or otherwise incorporates, noise reduction circuitry 203. The noise reduction circuitry 203 operates to improve the SNR of sensed cardiac signals by removing noise content of the sensed cardiac signals introduced from various sources. Typical types of transthoracic cardiac signal noise includes electrical noise and noise produced from skeletal muscles, for example. A number of methodologies for improving the SNR of sensed cardiac signals in the presence of skeletal muscular induced noise, including signal separation techniques incorporating combinations of electrodes and noise canceling multi-element electrodes, are described hereinbelow.

Detection circuitry 202 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 202 to detect and verify the presence and severity of an arrhythmic episode. Exemplary arrhythmia detection and discrimination circuitry, structures, and techniques, aspects of which may be implemented by an ITCS device of a type that may benefit from noise canceling electrode configurations, are disclosed in commonly owned U.S. Pat. Nos. 5,301,677 and 6,438,410, which are hereby incorporated herein by reference in their respective entireties. Arrhythmia detection methodologies particularly well suited for implementation in subcutaneous cardiac monitoring and/or stimulation systems are described hereinbelow.

The detection circuitry 202 communicates cardiac signal information to the control system 205. Memory circuitry 209 of the control system 205 contains parameters for operating in various sensing, defibrillation, and, if applicable, pacing modes, and stores data indicative of cardiac signals received by the detection circuitry 202. The memory circuitry 209 may also be configured to store historical ECG and therapy data, which may be used for various purposes and transmitted to an external receiving device as needed or desired.

In certain configurations, the ITCS device may include diagnostics circuitry 210. The diagnostics circuitry 210 typically receives input signals from the detection circuitry 202 and the sensing circuitry 204. The diagnostics circuitry 210 provides diagnostics data to the control system 205, it being understood that the control system 205 may incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the subcutaneous electrode(s) 214 and the can or indifferent electrode 207 of the ITCS device housing. Upon command, the shock therapy circuitry 216 delivers cardioversion and defibrillation stimulation energy to the heart in accordance with a selected cardioversion or defibrillation therapy. In a less sophisticated configuration, the shock therapy circuitry 216 is controlled to deliver defibrillation therapies, in contrast to a configuration that provides for delivery of both cardioversion and defibrillation therapies. Exemplary ICD high energy delivery circuitry, structures and functionality, aspects of which may be incorporated in an ITCS device of a type that may benefit from aspects of the present invention are disclosed in commonly owned U.S. Pat. Nos. 5,372,606; 5,411,525; 5,468,254; and 5,634,938, which are hereby incorporated herein by reference in their respective entireties.

In accordance with another configuration, an ITCS device may incorporate a cardiac pacing capability in addition to cardioversion and/or defibrillation capabilities. As is shown in dotted lines in FIG. 1C, the ITCS device may include pacing therapy circuitry 230, which is coupled to the control system 205 and the subcutaneous and can/indifferent electrodes 214, 207. Upon command, the pacing therapy circuitry delivers pacing pulses to the heart in accordance with a selected pacing therapy. Control signals, developed in accordance with a pacing regimen by pacemaker circuitry within the control system 205, are initiated and transmitted to the pacing therapy circuitry 230 where pacing pulses are generated. A pacing regimen may be modified by the control system 205.

A number of cardiac pacing therapies may be useful in a transthoracic cardiac monitoring and/or stimulation device. Such cardiac pacing therapies may be delivered via the pacing therapy circuitry 230 as shown in FIG. 1C. Alternatively, cardiac pacing therapies may be delivered via the shock therapy circuitry 216, which effectively obviates the need for separate pacemaker circuitry.

The ITCS device shown in FIG. 1C may be configured to receive signals from one or more physiologic and/or non-physiologic sensors. Depending on the type of sensor employed, signals generated by the sensors may be communicated to transducer circuitry coupled directly to the detection circuitry 202 or indirectly via the sensing circuitry 204. It is noted that certain sensors may transmit sense data to the control system 205 without processing by the detection circuitry 202.

Communications circuitry 218 is coupled to the microprocessor 206 of the control system 205. The communications circuitry 218 allows the ITCS device to communicate with one or more receiving devices or systems situated external to the ITCS device. By way of example, the ITCS device may communicate with a patient-worn, portable or bedside communication system via the communications circuitry 218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the ITCS device via the communications circuitry 218. It is noted that physiologic or non-physiologic sensors equipped with wireless transmitters or transceivers may communicate with a receiving system external of the patient.

The communications circuitry 218 may allow the ITCS device to communicate with an external programmer. In one configuration, the communications circuitry 218 and the programmer unit (not shown) use a wire loop antenna and a radio frequency telemetric link, as is known in the art, to receive and transmit signals and data between the programmer unit and communications circuitry 218. In this manner, programming commands and data are transferred between the ITCS device and the programmer unit during and after implant. Using a programmer, a physician is able to set or modify various parameters used by the ITCS device. For example, a physician may set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. The communications circuitry 218, or separate receiver circuitry, is configured to receive RF energy transmitted by an external RF energy transmitter. The ITCS device may, in addition to a rechargeable power source, include a non-rechargeable battery. It is understood that a rechargeable power source need not be used, in which case a long-life non-rechargeable battery is employed.

Figure 1D:
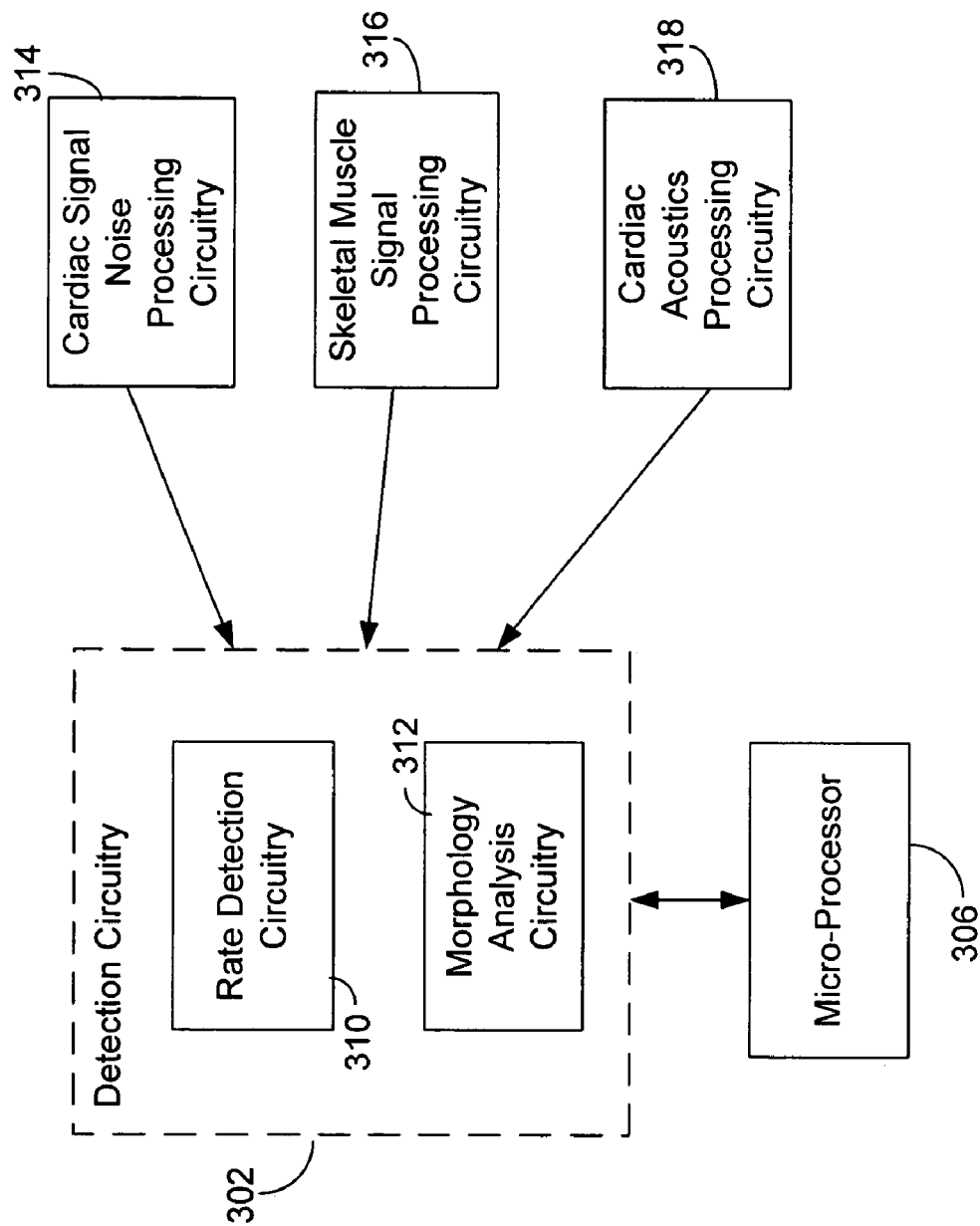
FIG. 1D is a block diagram illustrating various processing and detection components of a transthoracic cardiac sensing and/or stimulation device in accordance with an embodiment of the present invention.

FIG. 1D illustrates a configuration of detection circuitry 302 of an ITCS device, which includes one or both of rate detection circuitry 310 and morphological analysis circuitry 312. Detection and verification of arrhythmias may be accomplished using rate-based discrimination algorithms as known in the art implemented by the rate detection circuitry 310. Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference in their respective entireties.

The detection circuitry 302, which is coupled to a microprocessor 306, may be configured to incorporate, or communicate with, specialized circuitry for processing sensed cardiac signals in manners particularly useful in a transthoracic cardiac sensing and/or stimulation device. As is shown by way of example in FIG. 1D, the detection circuitry 302 may receive information from multiple physiologic and non-physiologic sensors. As illustrated, transthoracic acoustics may be monitored using an appropriate acoustic sensor. Heart sounds, for example, may be detected and processed by cardiac acoustic processing circuitry 318 for a variety of purposes. The acoustics data is transmitted to the detection circuitry 302, via a hardwire or wireless link, and used to enhance cardiac signal detection. For example, acoustics may be used to discriminate normal cardiac sinus rhythm with electrical noise from potentially lethal arrhythmias, such as ventricular tachycardia or ventricular fibrillation.

The detection circuitry 302 may also receive information from one or more sensors that monitor skeletal muscle activity. In addition to cardiac activity signals, transthoracic electrodes readily detect skeletal muscle signals. Such skeletal muscle signals may be used to determine the activity level of the patient. In the context of cardiac signal detection, such skeletal muscle signals are considered artifacts of the cardiac activity signal, which may be viewed as noise. Processing circuitry 316 receives signals from one or more skeletal muscle sensors, and transmits processed skeletal muscle signal data to the detection circuitry 302. This data may be used to discriminate normal cardiac sinus rhythm with skeletal muscle noise from cardiac arrhythmias.

As was previously discussed, the detection circuitry 302 is coupled to, or otherwise incorporates, noise-processing circuitry 314. The noise processing circuitry 314 processes sensed cardiac signals to improve the SNR of sensed cardiac signals by reducing noise content of the sensed cardiac signals.

The components, functionality, and structural configurations depicted in FIGS. 1A–1D are intended to provide an understanding of various features and combination of features that may be incorporated in an ITCS device. It is understood that a wide variety of ITCS and other implantable cardiac monitoring and/or stimulation device configurations are contemplated, ranging from relatively sophisticated to relatively simple designs. As such, particular ITCS or cardiac monitoring and/or stimulation device configurations may include particular features as described herein, while other such device configurations may exclude particular features described herein.

In accordance with embodiments of the invention, an ITCS device may be implemented to include a subcutaneous electrode system that provides for one or both of cardiac sensing and arrhythmia therapy delivery. According to one approach, an ITCS device may be implemented as a chronically implantable system that performs monitoring, diagnostic and/or therapeutic functions. The ITCS device may automatically detect and treat cardiac arrhythmias. In one configuration, the ITCS device includes a pulse generator and one or more electrodes that are implanted subcutaneously in the chest region of the body, such as in the anterior thoracic region of the body. The ITCS device may be used to provide atrial and ventricular therapy for bradycardia and tachycardia arrhythmias. Tachyarrhythmia therapy may include cardioversion, defibrillation and anti-tachycardia pacing (ATP), for example, to treat atrial or ventricular tachycardia or fibrillation. Bradycardia therapy may include temporary post-shock pacing for bradycardia or asystole. Methods and systems for implementing post-shock pacing for bradycardia or asystole are described in commonly owned US Publication No. 2004/0172066, which is incorporated herein by reference in its entirety.

In one configuration, an ITCS device according to one approach may utilize conventional pulse generator and subcutaneous electrode implant techniques. The pulse generator device and electrodes may be chronically implanted subcutaneously. Such an ITCS may be used to automatically detect and treat arrhythmias similarly to conventional implantable systems. In another configuration, the ITCS device may comprise a unitary structure (e.g., a single housing/unit). The electronic components and electrode conductors/connectors are disposed within or on the unitary ITCS device housing/electrode support assembly.

The ITCS device contains the electronics and may be similar to a conventional implantable defibrillator. High voltage shock therapy may be delivered between two or more electrodes, one of which may be the pulse generator housing (e.g., can), placed subcutaneously in the thoracic region of the body.

Additionally or alternatively, the ITCS device may also provide lower energy electrical stimulation for bradycardia therapy. The ITCS device may provide brady pacing similarly to a conventional pacemaker. The ITCS device may provide temporary post-shock pacing for bradycardia or asystole. Sensing and/or pacing may be accomplished using sense/pace electrodes positioned on an electrode subsystem also incorporating shock electrodes, or by separate electrodes implanted subcutaneously.

The ITCS device may detect a variety of physiological signals that may be used in connection with various diagnostic, therapeutic or monitoring implementations. For example, the ITCS device may include sensors or circuitry for detecting respiratory system signals, cardiac system signals, and signals related to patient activity. In one embodiment, the ITCS device senses intrathoracic impedance, from which various respiratory parameters may be derived, including, for example, respiratory tidal volume and minute ventilation. Sensors and associated circuitry may be incorporated in connection with an ITCS device for detecting one or more body movement or body position related signals. For example, accelerometers and GPS devices may be employed to detect patient activity, patient location, body orientation, or torso position.

The ITCS device may be used within the structure of an advanced patient management (APM) system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, can incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

An ITCS device according to one approach provides an easy to implant therapeutic, diagnostic or monitoring system. The ITCS system may be implanted without the need for intravenous or intrathoracic access, providing a simpler, less invasive implant procedure and minimizing lead and surgical complications. In addition, this system would have advantages for use in patients for whom transvenous lead systems cause complications. Such complications include, but are not limited to, surgical complications, infection, insufficient vessel patency, complications associated with the presence of artificial valves, and limitations in pediatric patients due to patient growth, among others. An ITCS system according to this approach is distinct from conventional approaches in that it is preferably configured to include a combination of two or more electrode subsystems that are implanted subcutaneously in the anterior thorax.

Figure 2:
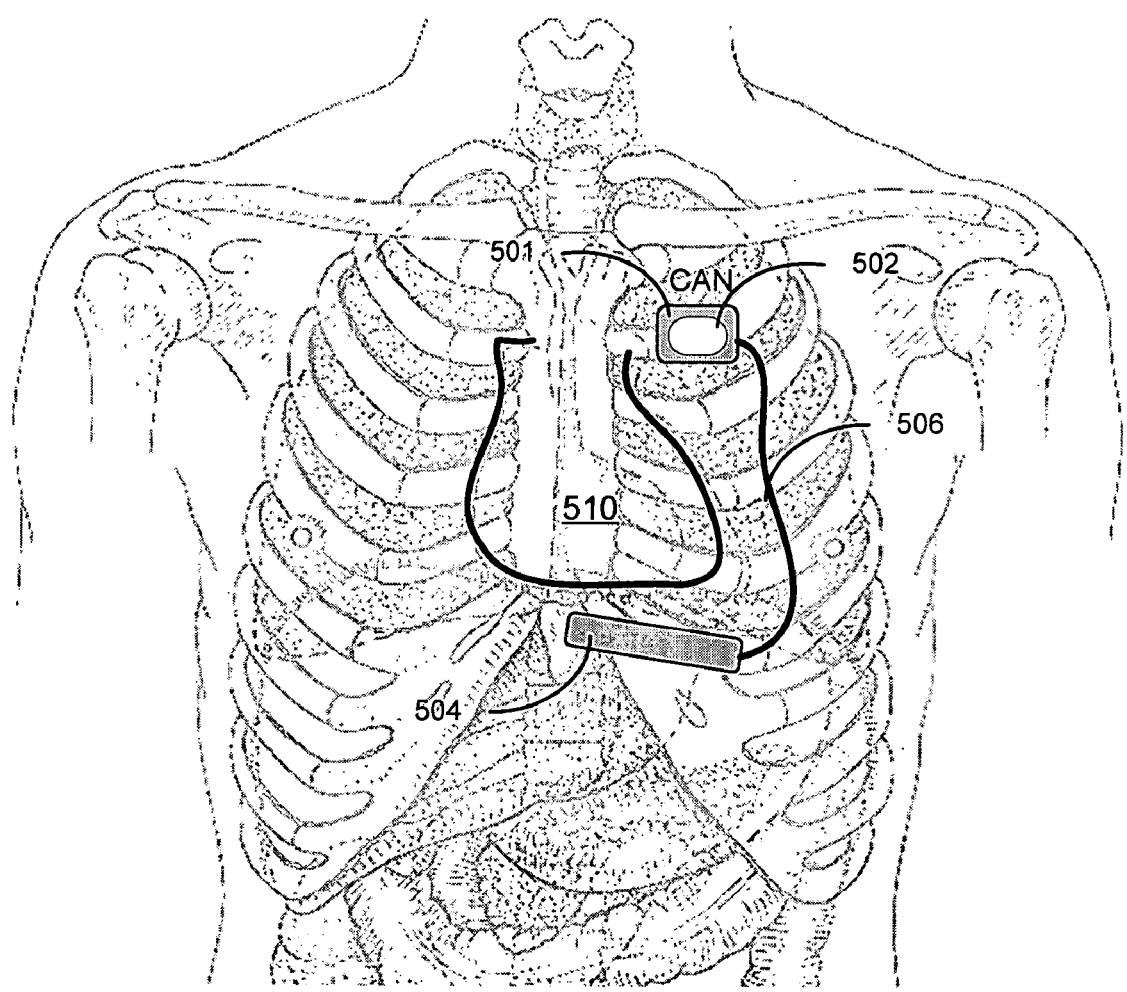
FIG. 2 is a diagram illustrating components of a transthoracic cardiac sensing and/or stimulation device including an electrode array in accordance with an embodiment of the present invention.

In one configuration, as is illustrated in FIG. 2, electrode subsystems of an ITCS system are arranged about a patient's heart 510. The ITCS system includes a first electrode subsystem, comprising a can electrode 502, and a second electrode subsystem 504 that includes at least two electrodes or at least one multi-element electrode. The second electrode subsystem 504 may comprise a number of electrodes used for sensing and/or electrical stimulation.

In various configurations, the second electrode subsystem 504 may comprise a combination of electrodes. The combination of electrodes of the second electrode subsystem 504 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 502 is positioned on the housing 501 that encloses the ITCS device electronics. In one embodiment, the can electrode 502 comprises the entirety of the external surface of the housing 501. In other embodiments, various portions of the housing 501 may be electrically isolated from the can electrode 502 or from tissue. For example, the active area of the can electrode 502 may comprise all or a portion of either the anterior or posterior surface of the housing 501 to direct current flow in a manner advantageous for cardiac sensing and/or stimulation.

In accordance with one embodiment, the housing 501 may resemble that of a conventional implantable ICD, and is approximately 20–100 cc in volume, with a thickness of 0.4 to 2 cm and with a surface area on each face of approximately 30 to 100 $cm^2$. As previously discussed, portions of the housing may be electrically isolated from tissue to optimally direct current flow. For example, portions of the housing 501 may be covered with a non-conductive, or otherwise electrically resistive, material to direct current flow. Suitable non-conductive material coatings include those formed from silicone rubber, polyurethane, or parylene, for example.

In addition, or alternatively, all or portions of the housing 501 may be treated to change the electrical conductivity characteristics thereof for purposes of optimally directing current flow. Various known techniques may be employed to modify the surface conductivity characteristics of the housing 501, such as by increasing or decreasing surface conductivity, to optimize current flow. Such techniques may include those that mechanically or chemically alter the surface of the housing 501 to achieve desired electrical conductivity characteristics.

As was discussed above, cardiac signals collected from subcutaneously implanted electrodes may be corrupted by noise. In addition, certain noise sources have frequency characteristics similar to those of the cardiac signal. Such noise may lead to over sensing and spurious shocks. Due to the possibility of relatively high amplitude of the noise signal and overlapping frequency content, filtering alone does not lead to complete suppression of the noise. In addition, filter performance is not generally sufficiently robust against the entire class of noises encountered. Further, known adaptive filtering approaches require a reference signal that is often unknown for situations when a patient experiences VF or high amplitude noise.

An ITCS device according to the present invention may be implemented to include a noise rejection/reduction capability to improve noise rejection of cardiac signals sensed by subcutaneous electrodes. This noise rejection/reduction approach advantageously reduces the risk of false positives for detection algorithms by improving the signal to noise ratio of the cardiac signal.

In accordance with one approach of the present invention, an ITCS device may be implemented to separate cardiac signals from noise in a robust manner using a blind source separation (BSS) technique. It is understood that all or certain aspects of the BSS technique described below may be implemented in a device or system (implantable or non-implantable) other than an ITCS device, and that the description of BSS techniques implemented in an ITCS device is provided for purposes of illustration, and not of limitation. For example, algorithms that implement a BSS technique as described below may be implemented for use by an implanted processor or a non-implanted processor, such as a processor of a programmer or computer.

Referring now to FIGS. 3 through 6, subcutaneous cardiac sensing and/or stimulation devices and methods employing cardiac signal separation are described in accordance with the present invention. The main principle of signal separation works on the premise that spatially distributed electrodes collect components of a signal from a common origin (e.g., the heart) with the result that these components will be strongly correlated to each other in time. In addition, these components will also be weakly correlated to components of another origin (e.g., noise). The ITCS device may be implemented to separate these components according to their sources. To achieve this, the methods and algorithms illustrated in FIGS. 3 through 6 may be implemented.

Figure 3:
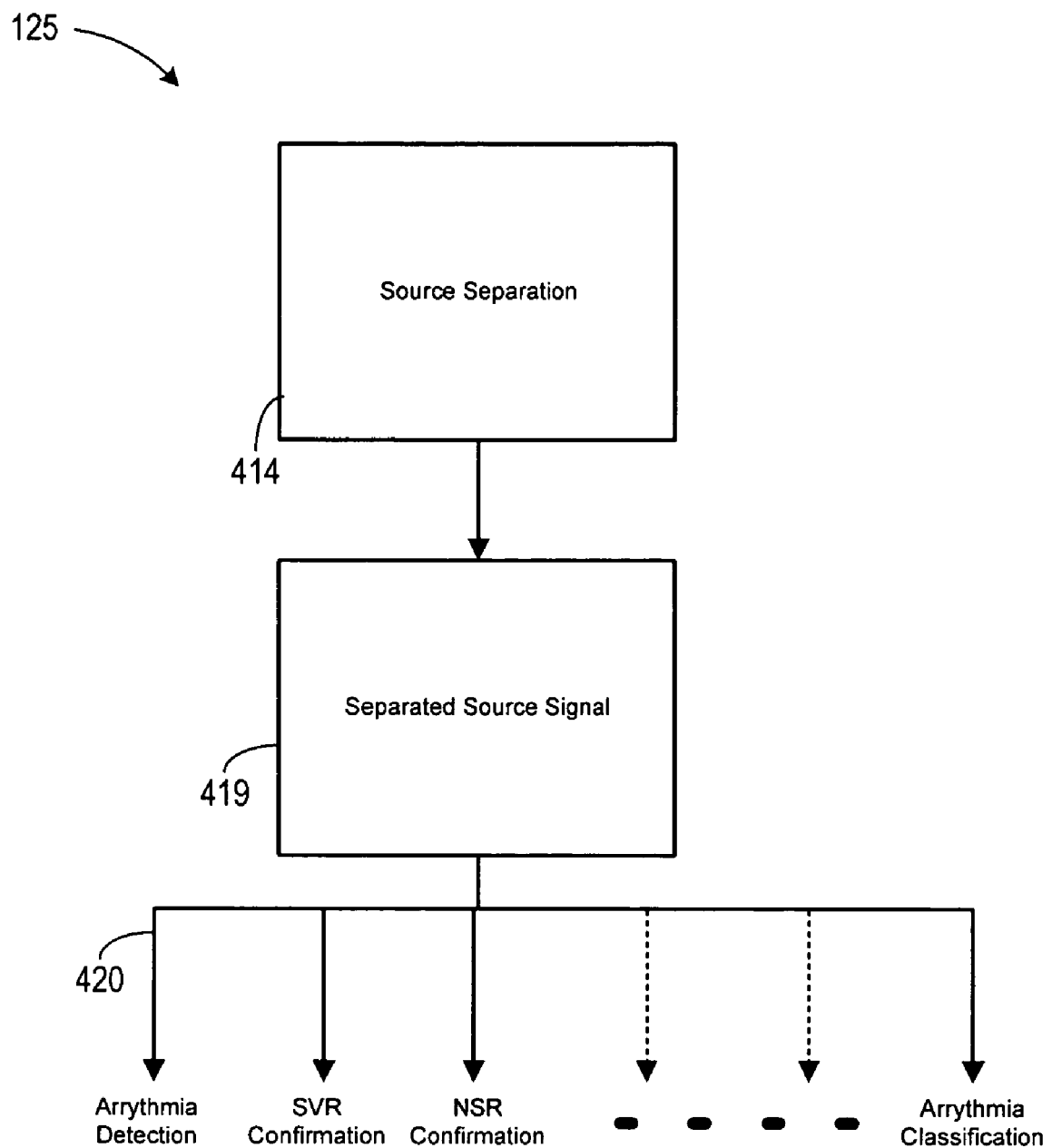
FIG. 3 is a block diagram illustrating uses of signal separation in accordance with the present invention.

FIG. 3 illustrates a source separation system 125 in accordance with the present invention. A source separation process 414 is performed, providing a separated signal 419. The separated signal 419 is available for a variety of uses 420, such as, for example, arrhythmia detection, SVR (Supra-Ventricular Rhythm) confirmation, NSR (Normal Sinus Rhythm) confirmation, arrhythmia classification or other use.

Figure 4:
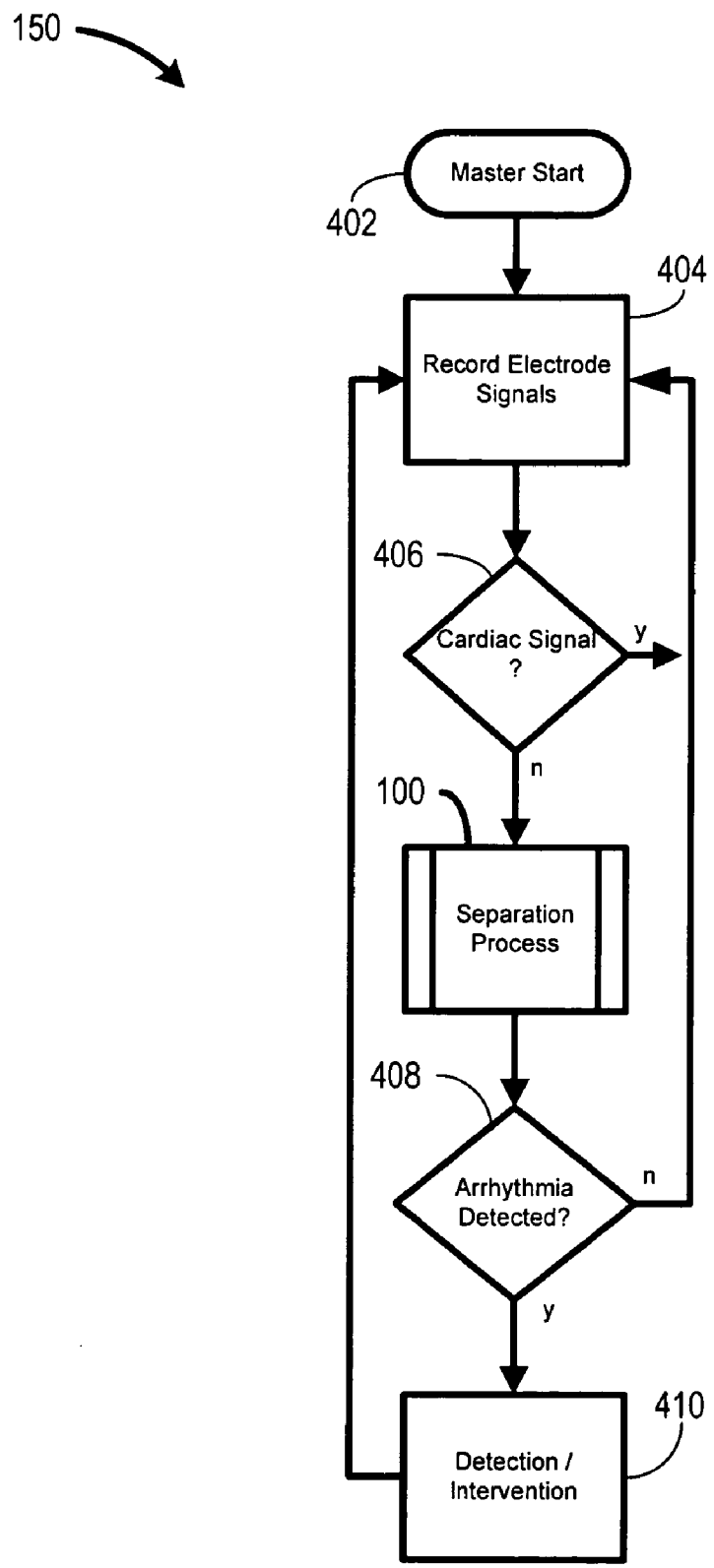
FIG. 4 is a block diagram of a cardiac sensing methodology incorporating signal separation in accordance with the present invention.

FIG. 4 illustrates a signal source separation methodology 150 in accordance with the present invention. After initiating 402 the methodology, a signal record process begins 404. During the signal record event 404, one or more electrode signals are recorded for later processing, such as by signal source separation processing. The recording may be continuous or performed for a given period of time. At block 406, a determination is made as to the presence or absence of an SVR using technology known in the art. If an SVR is detected, no other action is necessary, and recording and evaluation for SVR continues.

If SVR is absent, it is desirable to determine whether an adverse cardiac condition exists, necessitating intervention, or whether there is simply a spurious signal loss or other event not necessitating intervention. A loss of SVR at decision 406 initiates a separation process 100, which will be described in greater detail below. After the separation process 100 and any intervention steps deemed necessary are completed, a determination 408 is made as to whether other processing is necessary. If no further processing is necessary, the recording process 404 continues. If further processing is necessary, such additional processing 410 is performed, along with any further action associated with processing 410, and then recording 404 continues.

Figure 5:
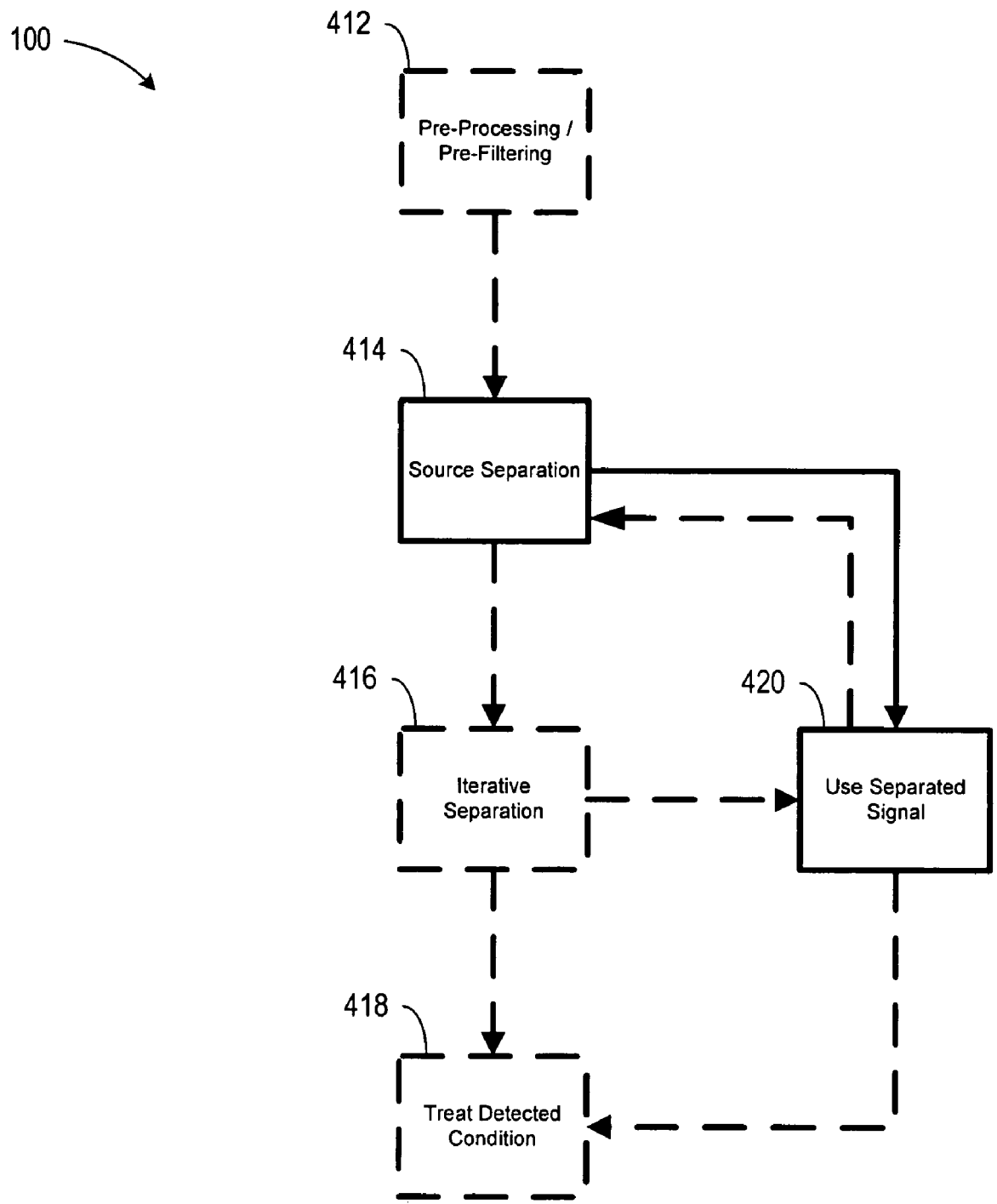
FIG. 5 is a block diagram of a signal separation process in accordance with the present invention.

FIG. 5 illustrates another embodiment of a signal source separation process 100 in accordance with the present invention. A set of composite signals, including at least two and up to n signals, are selected for separation, where n is an integer. Each electrode provides a composite signal associated with an unknown number of sources. Pre-processing and/or pre-filtering 412 can be performed on each of the composite signals. It may be advantageous to filter each composite signal using the same filtering function. Source separation 414 is performed, providing at least one separated signal. The separated signal can then be used 420 for some specified purpose, such as, for example, to confirm a normal sinus rhythm, determine a cardiac condition, define a noise signal, or other desired use.

If a treatment is desired, an appropriate treatment or therapy 418 is performed. If continued source separation is desired, the process returns to perform such source separation 414 and may iteratively separate 416 more signals until a desired signal is found, or all signals are separated.

Figure 6:
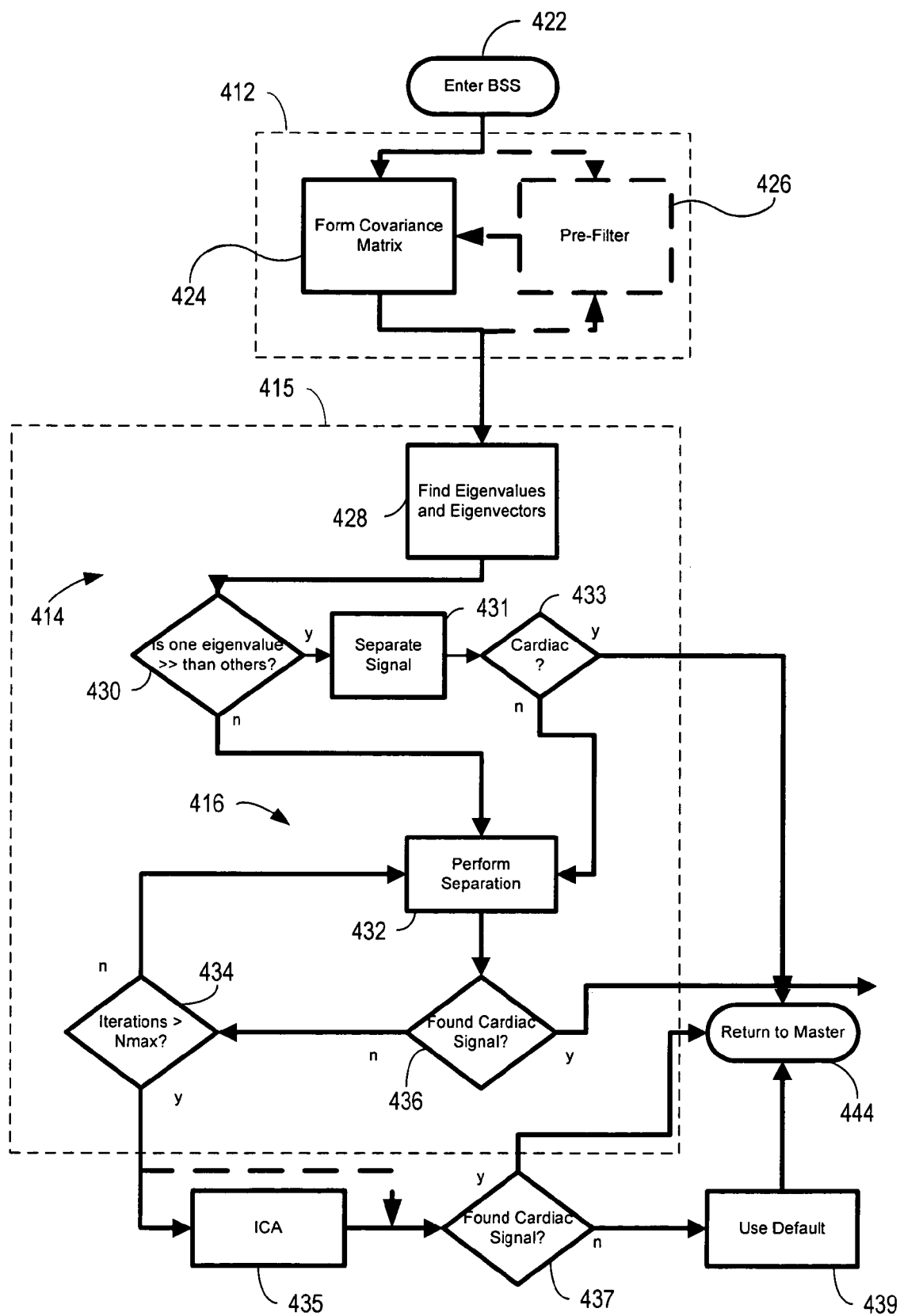
FIG. 6 is an expanded block diagram of the process illustrated in FIG. 5, illustrating an iterative independent component analysis in accordance with the present invention.

FIG. 6 illustrates further embodiments of a signal source separation process in greater detail, including some optional elements. Entry of the process at block 422 provides access to a pre-processing facility 412, illustrated here as including a covariance matrix computation block 424 and/or a pre-filtering block 426, such as, for example, a band-pass filtering block. The composite signals processed at pre-processing block 412 are provided to a signal source separation block 415, which can include functionality of the source separation block 414 and iterative source separation block 416 shown in FIG. 5.

The signal source separation block 415 includes a principal component analysis block 428, which produces an associated set of eigenvectors and eigenvalues using a covariance matrix or composite signals provided by pre-processing block 412. A determination 430 is made as to whether one eigenvalue is significantly larger than any others in the set, making the dimension associated with this eigenvalue a likely candidate for association with the cardiac signal. If such a candidate is identified at block 430, the candidate signal may immediately be separated 431 and a determination 433 made to confirm whether the candidate signal is a cardiac signal, before returning 444 to the master ITCS routine that called the signal source separation process.

If there is no clear candidate eigenvalue, or if the largest value eigenvalue did not provide a signal of interest, an iterative process may be used to separate 432 and search 436 for the signal of interest (e.g., cardiac signal). This process 432, 436, 434 can be repeated until such a signal is found, or no more signals are separable 434 as determined by exceeding a predefined number of iterations $N_{max}$ or some other termination criterion. An example of such a criterion is an eigenvalue considered at the current iteration being proportionately smaller than the largest eigenvalues by some predetermined amount.

If the iterations 434 are completed and a cardiac signal is not found at 436, then an Independent Component Analysis 435 may be attempted to further process the signals in an attempt to find the cardiac signal. If a cardiac signal is still not found at decision 437, after exhausting all possibilities, then a set of default settings 439 may be used, or an error routine may be initiated.

With continued reference to FIGS. 3 through 6, one illustrative signal source separation methodology according to the present invention is described below. Such an approach is particularly well-suited for use in an ITCS system. It is to be understood that the example provided below is provided for non-limiting, illustrative purposes only. Moreover, it is understood that signal source separation within the context of the present invention need not be implemented using the specific processes described below, or each and every process described below.

A collected signal is preferably pre-filtered to suppress broadly incoherent noise and to generally optimize the signal-to-noise ratio (SNR). Any noise suppression in this step has the additional benefit of reducing the effective number of source signals that need to be separated.

A Principal Component Analysis (PCA) is performed on the collected and/or pre-filtered signal, producing a set of eigenvectors and associated eigenvalues describing the optimal linear combination, in a least-squares sense, of the recorded signals that makes the components coming from different sources orthogonal to one another. As an intermediate step to performing the PCA, an estimate of the spatial covariance matrix may be computed and averaged over a relatively short time interval (on the order of 2–3 beats) to enhance those components that are mutually correlated.

Each eigenvalue corresponds to the power of the signal projected along the direction of each associated eigenvector. The cardiac signal component is typically identified by one of the largest eigenvalues. Occasionally, PCA does not achieve a substantially sufficient level of source independence. In such a case, an Independent Component Analysis (ICA) may be performed to determine the actual source direction, either upon the PCA-transformed signal, or directly upon the collected signal. The ICA consists of a unitary transformation based on higher-order statistical analysis. For example, separation of two mixed sources may be achieved by rotating the complex variable formed from the signals on an angle that aligns their probability distributions with basis vectors. In another approach, an algorithm based on minimization of mutual information between components, as well as other approaches generally known in the field of ICA, may be used to achieve reconstructed source independence.

Figure 7:
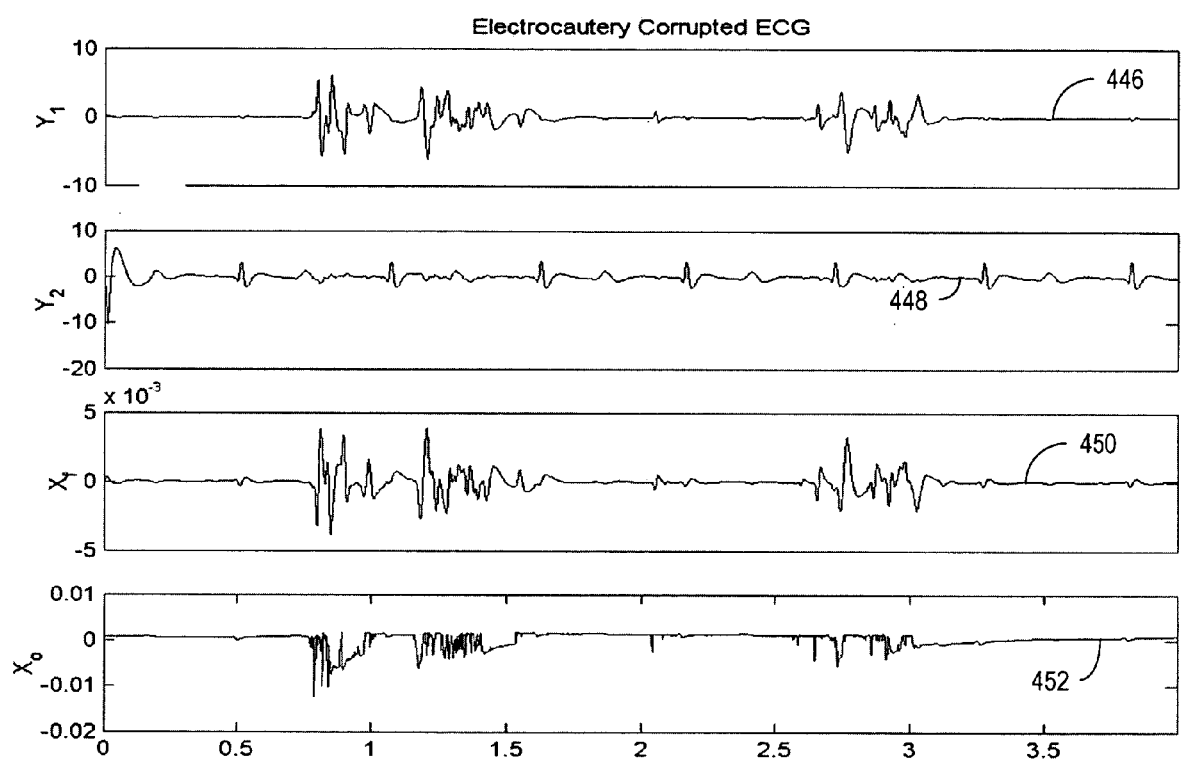
FIG. 7 is a graph illustrating the results of a signal separation process in accordance with the present invention.

FIG. 7 graphically depicts SNR improvement achievable by a signal source separation methodology of the present invention. In this illustrative example, data was gathered under low-SNR conditions with electrocautery noise using seven electrodes implanted in the thoracic region of a pig. The bottom subplot, identified as trace 452, represents the raw implanted electrode signal. The next subplot, identified as trace 450, shows this signal after input filtering for optimal raw SNR using a linear-phase ($4^{th}$-order Bessel) band pass filter from 5 to 20 Hz. The top two subplots, identified as trace 448 and trace 446, illustrate the resulting separated components associated with the two largest eigenvalues. In this example, trace 446 is associated with the electrocautery signal, having the largest eigenvalue. Trace 448 is the uncorrupted cardiac signal.

An ITCS device may, for example, employ a hierarchical decision-making procedure that initiates a blind source separation algorithm when noise or arrhythmia is detected. By way of example, a local peak density algorithm or a curvature-based significant point methodology may be used as a high-level detection routine.

The ITCS device may compute an estimate of the covariance matrix. It may be sufficient to compute the covariance matrix for only a short time. Computation of the eigenvalues and eigenvectors required for the PCA may also be performed adaptively through an efficient updating algorithm.

The cardiac signal can be identified among the few (e.g., two or three) largest separated signals. One of several known algorithms may be used. For example, local peak density (LPD) or beat detection (BD) algorithms may be used. The LPD algorithm can be used to identify the cardiac signal by finding a signal that has an acceptable physiologic range of local peak densities by comparing the LPD to a predetermined range of peak densities known to be acceptable. The BD algorithm will find a signal that has a physiologic range of beat rate. In the case where two signals look similar, a morphology algorithm may be used for further discrimination. It may be beneficial to use the same algorithm at different levels of hierarchy: 1) initiation of blind source separation algorithm; 2) iterative identification of a cardiac signal.

Mathematical development of an exemplary blind source separation algorithm in accordance with the present invention is provided as follows. Assume there are m source signals $s_1(t), \ldots, s_m(t)$ that are detected inside of the body, comprising a desired cardiac signal and some other independent noise, which may, for example, include myopotential noise, electrocautery response, etc. These signals are recorded simultaneously from k sensing vectors derived from subcutaneous sensing electrodes, where k>m in a preferred approach. By definition, the signals are mixed together into the overall voltage gradient sensed across the electrode array. In addition, there is usually an additive noise attributable, for example, to environmental noise sources. The relationship between the source signals s(t) and recorded signals x(t) is described below:

$$\begin{pmatrix} x_1(t) \\ x_2(t) \\ \vdots \\ x_k(t) \end{pmatrix} = \begin{pmatrix} y_1(t) \\ y_2(t) \\ \vdots \\ y_k(t) \end{pmatrix} + \begin{pmatrix} n_1(t) \\ n_2(t) \\ \vdots \\ n_k(t) \end{pmatrix}$$

$$= \begin{pmatrix} a_{11} & a_{12} & \ldots & a_{1m} \\ a_{21} & a_{22} & \ldots & a_{2m} \\ \vdots & \vdots & \ddots & \vdots \\ a_{k1} & a_{k2} & \ldots & a_{km} \end{pmatrix} \begin{pmatrix} s_1(t) \\ s_2(t) \\ \vdots \\ s_m(t) \end{pmatrix} + \begin{pmatrix} n_1(t) \\ n_2(t) \\ \vdots \\ n_k(t) \end{pmatrix}$$

$$= x(t)$$
$$= y(t) + n(t)$$
$$= As(t) + n(t), \quad m < k$$

Here, x(t) is an instantaneous linear mixture of the source signals and additive noise, y(t) is the same linear mixture without the additive noise, n(t) is environmental noise modeled as Gaussian noise, A is an unknown mixing matrix, and s(t) are the unknown source signals considered here to comprise the desired cardiac signal and other biological artifacts. There is no assumption made about the underlying structure of the mixing matrix and the source signals, except for their spatial statistical independence. The objective is to reconstruct the source signals s(t) from the recorded signals x(t).

Reconstruction of the source signals s(t) from the recorded signals x(t) preferably involves pre-filtering x(t) to optimize the SNR (i.e., maximize the power of s(t) against that of n(t)). Here, a linear phase filter can be used to minimize time-domain dispersion (tails and ringing) and best preserve the underlying cardiac signal morphology. It is noted that the notation x(t) is substituted for the pre-filtered version of x(t).

An estimate of the spatial covariance matrix R is formed as shown immediately below. This step serves to enhance the components of the signal that are mutually correlated and downplays incoherent noise.

$$R = \frac{1}{T_{(\sim 1\,\text{sec})}} \sum_{t=1,T} \begin{pmatrix} x_1(t) \\ x_2(t) \\ \ldots \\ x_k(t) \end{pmatrix} * (x_1(t) \; x_2(t) \; \ldots \; x_k(t))$$

$$= \frac{1}{T_{(\sim 1\,\text{sec})}} \sum_{t=1,T} \begin{bmatrix} x_1(t)*x_1(t) & x_1(t)*x_2(t) & \ldots & x_1(t)*x_k(t) \\ x_2(t)*x_1(t) & x_2(t)*x_2(t) & \ldots & x_2(t)*x_k(t) \\ \ldots & \ldots & \ddots & \ldots \\ x_k(t)*x_1(t) & x_k(t)*x_2(t) & \ldots & x_k(t)*x_k(t) \end{bmatrix}$$

Eigenvalues and eigenvectors of the covariance matrix R may be determined using singular value decomposition (SVD). By definition, the SVD factors R as a product of three matrices $R=USV^T$, where U and V are orthogonal matrices describing amplitude preserving rotations, and S is a diagonal matrix that has the squared eigenvalues $\sigma_1 \ldots \sigma_k$ on the diagonal in monotonically decreasing order. Expanded into elements, this SVD may be expressed as follows.

$$R = \begin{pmatrix} u_{11} & u_{12} & \ldots & u_{1k} \\ u_{21} & u_{22} & \ldots & u_{2k} \\ \vdots & \vdots & \ddots & \vdots \\ u_{k1} & u_{k2} & \ldots & u_{kk} \end{pmatrix} \begin{pmatrix} \sigma_1 & 0 & 0 & 0 \\ 0 & \sigma_2 & 0 & 0 \\ \vdots & \vdots & \ddots & \vdots \\ 0 & 0 & \ldots & \sigma_k \end{pmatrix} \begin{pmatrix} v_{11} & v_{12} & \ldots & v_{1k} \\ v_{21} & v_{22} & \ldots & v_{2k} \\ \vdots & \vdots & \ddots & \vdots \\ v_{k1} & v_{k2} & \ldots & v_{kk} \end{pmatrix}$$

The columns of matrix V consist of eigenvectors that span a new coordinate system wherein the components coming from different sources are orthogonal to one another. Eigenvalues $\sigma_1 \ldots \sigma_k$ correspond respectively to columns 1 ... k of V. Each eigenvalue defines the signal "power" along the direction of its corresponding eigenvector. The matrix V thus provides a rotational transformation of x(t) into a space where each separate component of x is optimally aligned, in a least-squares sense, with a basis vector of that space.

The largest eigenvalues correspond to the highest power components, which typically represent the mixed source signals $y_1(t), \ldots, y_m(t)$. The lower eigenvalues typically are associated with additive noise $n_1(t), \ldots, n_{k-m}(t)$. Each eigenvector may then be viewed as an optimal linear operator on x that maximizes the power of the corresponding independent signal component. As a result, the transformed signal is found as:

$$\hat{y}(t) = \begin{pmatrix} \hat{y}_1(t) \\ \vdots \\ \hat{y}_m(t) \end{pmatrix} = \begin{pmatrix} v_{11} & v_{21} & \ldots & v_{k1} \\ \vdots & \vdots & \ddots & \vdots \\ v_{1m} & v_{2m} & \ldots & v_{km} \end{pmatrix} * \begin{pmatrix} x_1(t) \\ x_2(t) \\ \vdots \\ x_k(t) \end{pmatrix}$$

The component estimates $\hat{y}_1(t), \ldots, \hat{y}_m(t)$ of $y_1(t), \ldots, y_m(t)$ are aligned with the new orthogonal system of coordinates defined by eigenvectors. As a result, they should be orthogonal to each other and thus independent.

In an alternative implementation, eigenvalues and eigenvectors of the covariance matrix R may be determined using eigenvalue decomposition (ED). By definition, the ED solves the matrix equation RV=SV so that S is a diagonal matrix having the eigenvalues $\sigma_1 \ldots \sigma_k$ on the diagonal, preferably in monotonically decreasing order, and so that matrix V contains the corresponding eigenvectors along its columns. The resulting eigenvalues and associated eigenvectors may be applied in similar manner to those resulting from the SVD of covariance matrix R.

In an alternative implementation, eigenvalues and eigenvectors are computed directly from x(t) by forming a rectangular matrix X of k sensor signals collected during a time segment of interest, and performing an SVD directly upon X. The matrix X and its decomposition may be expressed as follows.

$$X = \begin{pmatrix} x_1(t) \\ x_2(t) \\ \vdots \\ x_k(t) \end{pmatrix} = \begin{pmatrix} x_1(t_1) & x_1(t_2) & \cdots & x_1(t_T) \\ x_2(t_1) & x_2(t_2) & \cdots & x_2(t_T) \\ \vdots & \vdots & \ddots & \vdots \\ x_k(t_1) & x_k(t_2) & \cdots & x_k(t_T) \end{pmatrix} = USV^T$$

Note that in cases where T>k, a so-called "economy-size" SVD may be used to find the eigenvalues and eigenvectors efficiently. Such an SVD may be expressed as follows, expanded into elements.

$$X = USV^T$$

$$= \begin{pmatrix} u_{11} & u_{12} & \cdots & u_{1T} \\ u_{21} & u_{22} & \cdots & u_{2T} \\ \vdots & \vdots & \ddots & \vdots \\ u_{k1} & u_{k2} & \cdots & u_{kT} \end{pmatrix} \begin{pmatrix} \sigma_1 & 0 & \cdots & 0 \\ 0 & \sigma_2 & \cdots & 0 \\ \vdots & \vdots & \ddots & \vdots \\ 0 & 0 & \cdots & \sigma_k \end{pmatrix} \begin{pmatrix} v_{11} & v_{12} & \cdots & v_{1k} \\ v_{21} & v_{22} & \cdots & v_{2k} \\ \vdots & \vdots & \ddots & \vdots \\ v_{k1} & v_{k2} & \cdots & v_{kk} \end{pmatrix}$$

A similar economy-sized SVD may also be used for the less typical case where k>T. The matrices S and V resulting from performing the SVD of data matrix X may be applied in the context of this present invention identically as the matrices S and V resulting from performing the SVD on the covariance matrix R.

At this point, the mutual separation of $\hat{y}_1(t), \ldots, \hat{y}_m(t)$ would be completed, based on the covariance statistics. Occasionally, information from covariance is not sufficient to achieve source independence. This happens, for example, when the cardiac signal is corrupted with electrocautery, which may cause perturbations from the linearly additive noise model. In such a case, Independent Component Analysis (ICA) can be used to further separate the signals.

The ICA seeks to find a linear transformation matrix W that inverts the mixing matrix A in such manner as to recover an estimate of the source signals. The operation may be described as follows.

$$s(t) = \begin{pmatrix} s_1(t) \\ s_2(t) \\ \vdots \\ s_m(t) \end{pmatrix} = W\, y(t) \approx A^{-1} y(t)$$

Here we substitute s(t) for the recovered estimate of the source signals. The signal vector y(t) corresponds to either the collected sensor signal vector x(t) or to the signal $\hat{y}(t)$ separated with PCA. The matrix W is the solution of an optimization problem that maximizes the independence between the components $s_1(t), \ldots, s_m(t)$ of s(t)=Wy(t). We treat the components of s(t) as a vector of random variables embodied in the vector notation s, so that the desired transformation would optimize some cost function $C(s)=C([s_1(t), \ldots, s_m(t)])$ that measures the mutual independence of these components. Given the joint probability density function (pdf) f(s) and the factorized pdf $\bar{f}(s)=f_1(s_1) f_2(s_2) \ldots f_m(s_m)$, or given estimates of these pdf's, we may solve the following.

$$\min_W C(s) = \min_W \int D(f(s), \bar{f}(s))ds$$

The function D(f (s), $\bar{f}(s)$) may be understood as a standard distance measure generally known in the art, such as for example an absolute value difference $|f(s)-\bar{f}(s)|$, Euclidean distance $(f(s)-\bar{f}(s))^2$, or p-norm $(f(s)-\bar{f}(s))^p$. The distance measure approaches zero as f(s) approaches $\bar{f}(s)$, which by the definition of statistical independence, occurs as the components of s approach mutual statistical independence.

In an alternative implementation, the distance measure may take the form of a Kullback-Liebler divergence (KLD) between f(s) and $\bar{f}(s)$, yielding cost function optimizations in either of the following forms.

$$\min_W C(s) = \min_W \int f(s) \log \frac{f(s)}{\bar{f}(s)} ds$$

or $$= \min_W \int \bar{f}(s) \log \frac{\bar{f}(s)}{f(s)} ds$$

Since the KLD is not symmetric, the two alternative measures are related but not precisely equal. One measure could be chosen, for example, if a particular underlying data distribution favors convergence with that measure.

Several alternative approaches may be used to measure the mutual independence of the components of s. These may include the maximum likelihood method, maximization of negentropy or its approximation, and minimization of mutual information.

In the maximum likelihood method, the desired matrix W is found as a solution of the following optimization problem, $$\max_W \sum_{j=1}^{T} \sum_{i=1}^{m} \log f_i(s_i(t_j)) + T \log|\det W| = \max_W \sum_{j=1}^{T} \sum_{i=1}^{m} \log f_i(w_i^T y(t_j)) + T \log|\det W|$$

where $w_i$ are columns of the matrix W. In the negentropy method, the cost function is defined in terms of differences in entropy between s and a corresponding Gaussian random variable, resulting in the following optimization problem, $$\max_W \{H(s_{gauss}) - H(s)\} =$$

$$\max_W \left\{ -\int f(s_{gauss}) \log f(s_{gauss}) ds_{gauss} + \int f(s) \log(s) ds \right\}$$

where H(s) is the entropy of random vector s, and $s_{gauss}$ is a Gaussian random vector chosen to have a covariance matrix substantially the same as that of s.

In the minimization of mutual information method, the cost function is defined in terms of the difference between the entropy of s and the sum of the individual entropies of the components of s, resulting in the following optimization problem.

$$\min_{W} \left\{ -\sum_{i=1}^{m} \int f(s_i) \log f(s_i) ds_i + \int f(s) \log f(s) ds \right\}$$

All preceding cost function optimizations having an integral form may be implemented using summations by approximating the underlying pdf s with discrete pdf's, for example as the result of estimating the pdf using well-known histogram methods. We note that knowledge of the pdf, or even an estimate of the pdf, can be difficult to implement in practice due either to computational complexity, sparseness of available data, or both. These difficulties may be addressed using cost function optimization methods based upon kurtosis, a statistical parameter that does not require a pdf.

In an alternative method, a measure of independence could be expressed via kurtosis, equivalent to the fourth-order statistic defined as the following for the $i^{th}$ component of s.

$$\text{kurt}(s_i) = E\{s_i^4\} - 3(E\{s_i^2\})^2$$

In this case W is found as a matrix that maximizes kurtosis of s=Wy over all the components of s (understanding y to be a vector of random variables corresponding to the components of y(t)). In all the previous examples of ICA optimization the solution W could be found via numerical methods such as steepest descent, Newton iteration, etc., well known and established in the art. These methods could prove numerically intensive to implement in practice, particularly if many estimates of statistics in s must be computed for every iteration in W.

Computational complexity can be addressed by several means. To begin, the ICA could be performed on the PCA-separated signal $\hat{y}(t)$ with the dimensionality reduced to only the first few (or in the simplest case, two) principal components. For situations where two principal components are not sufficient to separate the sources, the ICA could still be performed pairwise on two components at a time, substituting component pairs at each iteration of W (or group of iterations of W).

In one example, a simplified two-dimensional ICA may be performed on the PCA separated signals. In this case, a unitary transformation could be found as a Givens rotation matrix with rotation angle $\theta$, $$W(\theta) = \begin{pmatrix} \cos\theta & \sin\theta \\ -\sin\theta & \cos\theta \end{pmatrix}$$

where $s(t) = W(\theta)y(t)$. Here $W(\theta)$ maximizes the probability distribution of each component along the basis vectors, such that the following is satisfied.

$$\theta = \arg\max_{\theta} \sum_{t=1}^{T} \log f(s(t) | \theta)$$

This optimal rotation angle may be found by representing vectors y(t) and s(t)

$$\xi = e^{i4\theta} E(\rho^4 e^{i4\phi'}) = e^{i4\theta} E[(s_1 + is_2)^4] = e^{i4\theta}(\kappa_{40}^s + \kappa_{04}^s)$$

as complex variables in the polar coordinate form $y = y_1 + iy_2 = \rho e^{i\phi}$, $s = s_1 + is_2 = \rho e^{i\phi'}$ and finding the relationships between their phase angles $\phi$, $\phi'$: $\phi = \phi' + \theta$, where $\theta$ is the rotation that relates the vectors. Then, the angle $\theta$ may be found from the fourth order-statistic of a complex variable $\xi$, where $\kappa^s$ is kurtosis of the signal s(t).

By definition, source kurtosis is unknown, but may be found based on the fact that the amplitude of the source signal and mixed signals are the same.

As a result, $4\theta = \hat{\xi} \text{sign}(\hat{\gamma})$ with $\gamma = E[\rho^4] - 8 = \kappa_{40}^s + \kappa_{04}^s$ and $\rho^2 = s_1^2 + s_2^2 = y_1^2 + y_2^2$ In summary, the rotation angle can be estimated as:

$$\theta = \frac{1}{4} \text{angle}(\hat{\xi} \text{sign}(\hat{\gamma})) \text{ where}$$

$$\hat{\xi} = \frac{1}{T} \sum_{t=1,T} \rho_t^4 e^{i4\varphi(t)} = \frac{1}{T} \sum_{t=1,T} (y_1(t) + iy_2(t))^4,$$

$$\hat{\gamma} = \frac{1}{T} \sum_{t=1,T} \rho_t^4 - 8 = \frac{1}{T} \sum_{t=1,T} (y_1^2(t) + iy_2^2(t))^4 - 8$$

After the pre-processing step, the cardiac signal is normally the first or second most powerful signal. In addition, there is usually in practice only one source signal that is temporally white. In this case, rotation of the two-dimensional vector $y = y_1 + iy_2 = \rho e^{i\phi}$ is all that is required. In the event that more than two signals need to be separated, the Independent Component Analysis process may be repeated in pair-wise fashion over the $m(m-1)/2$ signal pairs until convergence is reached, usually taking about $(1+\sqrt{m})$iterations.

An ITCS device that implements the above-described processes may robustly separate the cardiac signal from a low SNR signal recorded from the implantable device. Such an ITCS device robustly separates cardiac signals from noise to allow for improved sensing of cardiac rhythms and arrhythmias.

The system operates by finding a combination of the spatially collected low SNR signals that makes cardiac signal and noise orthogonal to each other (independent). This combination achieves relatively clean extraction of the cardiac signal even from negative SNR conditions.

An ITCS device may operate in a batch mode or adaptively, allowing for on-line or off-line implementation. To save power, the system may include the option for a hierarchical decision-making routine that uses algorithms known in the art for identifying presence of arrhythmias or noise in the collected signal and turning on the cardiac signal extraction routine.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A signal separation method, comprising:
    detecting a plurality of composite signals at a plurality of subcutaneous non-intrathoracic locations, the plurality of composite signals associated with a plurality of sources;
    separating a signal from the plurality of composite signals using blind source separation; and
    identifying the separated signal as a cardiac signal.

2. The method of claim 1, further comprising iteratively separating signals from the plurality of composite signals until the cardiac signal is identified.

3. The method of claim 1, wherein the plurality of composite signals comprises the cardiac signal and at least one non-cardiac signal.

4. The method of claim 1, wherein the blind source separation comprises a principal component analysis.

5. The method of claim 4, wherein the principal component analysis includes a singular value decomposition.

6. The method of claim 4, wherein the principal component analysis includes an eigenvalue decomposition.

7. The method of claim 1, wherein the blind source separation comprises an independent component analysis.

8. The method of claim 1, wherein the blind source separation comprises a principal component analysis and an independent component analysis.

9. The method of claim 1, further comprising filtering each of the plurality of composite signals before separating the signal.

10. The method of claim 1, further comprising band-pass filtering each of the plurality of composite signals.

11. The method of claim 1, further comprising determining a cardiac condition using the cardiac signal.

12. The method of claim 1, further comprising detecting a cardiac condition using the separated signal, wherein detecting the cardiac condition comprises performing a rate based analysis of the cardiac signal.

13. The method of claim 1, further comprising detecting a cardiac condition using the separated signal, wherein detecting the cardiac condition comprises performing a morphology based analysis of the cardiac signal.

14. The method of claim 1, further comprising detecting a cardiac condition using the separated signal, wherein detecting the cardiac condition comprises performing a pattern and rate based analysis of the cardiac signal.

15. The method of claim 1, further comprising detecting a cardiac condition using the cardiac signal and implantably treating the cardiac condition.

16. The method of claim 15, wherein implantably treating the cardiac condition comprises delivering a cardiac stimulation therapy.

17. The method of claim 15, wherein implantably treating the cardiac condition comprises delivering a cardiac stimulation therapy using an implanted subcutaneous non-intrathoracic electrode.

18. The method of claim 15, wherein detecting the plurality of composite signals at the plurality of subcutaneous locations comprises using a subcutaneous non-intrathoracic electrode array and wherein implantably treating the cardiac condition comprises using the electrode array to provide a cardiac stimulation therapy.

19. The method of claim 1, further comprising:
    forming a composite signal matrix from the plurality of composite signals; and
    performing a principal component analysis on the composite signal matrix, thereby producing a set of eigenvalues and associated eigenvectors.

20. The method of claim 19, wherein an eigenvector of the associated eigenvectors that is associated with a largest magnitude eigenvalue of the set of eigenvalues is used to separate the signal from the plurality of composite signals.

21. The method of claim 20, wherein the signal is separated from the plurality of composite signals by multiplying the composite signal matrix by the eigenvector.

22. The method of claim 20, wherein the signal is separated iteratively from the plurality of composite signals using an eigenvector associated with a next-largest magnitude eigenvalue for each iteration, until the cardiac signal is identified.

23. The method of claim 22, wherein the cardiac signal is identified using a local peak density of the separated signal, wherein the local peak density is within a predetermined range.

24. The method of claim 22, wherein the cardiac signal is identified using beat detection on the separated signal, wherein a beat rate is within a predetermined range.

25. The method of claim 22, wherein the cardiac signal is identified using a local rate of occurrence of significant points in the separated signal, wherein the local rate of occurrence is within a predetermined range.

26. The method of claim 22, wherein the cardiac signal is identified using a morphology of the separated signal, wherein the morphology satisfies a physiological characteristic.

27. The method of claim 19, further comprising forming an intermediate signal matrix by multiplying the composite signal matrix by a matrix composed of the eigenvectors corresponding to at least the two largest eigenvalues, and finding a unitary matrix corresponding to a rotational transformation of the intermediate signal matrix that increases the independence of the intermediate signals.

28. The method of claim 27, further comprising forming an independent signal matrix by multiplying the intermediate signal matrix by the unitary matrix, wherein the independent signal matrix comprises a set of independent signal vectors.

29. The method of claim 28, wherein a signal vector from the set of independent signal vectors is iteratively examined until a cardiac signal is identified.

30. The method of claim 29, wherein the cardiac signal is identified using a local peak density of the examined signal, wherein the local peak density is within a predetermined range.

31. The method of claim 29, wherein the cardiac signal is identified using beat detection on the examined signal, wherein a beat rate is within a predetermined range.

32. The method of claim 29, wherein the cardiac signal is identified using a local rate of occurrence of significant points in the examined signal, wherein the local rate of occurrence is within a predetermined range.

33. The method of claim 29, wherein the cardiac signal is identified using a morphology of the examined signal, wherein the morphology satisfies a physiological characteristic.

34. The method of claim 1, further comprising forming an estimate of a spatial covariance matrix for a composite signal matrix formed from the plurality of composite signals.

35. The method of claim 34, further comprising performing a principal component analysis on the estimate of the spatial covariance matrix, producing a set of eigenvalues and associated eigenvectors.

36. The method of claim 35, wherein an eigenvector of the associated eigenvectors that is associated with a largest magnitude eigenvalue of the set of eigenvalues is used to separate the signal from the plurality of composite signals.

37. The method of claim 36, wherein the signal is separated from the plurality of composite signals by multiplying the composite signal matrix by the eigenvector.

38. The method of claim 36, wherein the signal is separated iteratively from the plurality of composite signals using an eigenvector associated with a next-largest magnitude eigenvalue for each iteration, until the cardiac signal is identified.

39. The method of claim 38, wherein the cardiac signal is identified using a local peak density of the separated signal, wherein the local peak density is within a predetermined range.

40. The method of claim 38, wherein the cardiac signal is identified using beat detection on the separated signal, wherein a beat rate is within a predetermined range.

41. The method of claim 38, wherein the cardiac signal is identified using a local rate of occurrence of significant points in the separated signal, wherein the local rate of occurrence is within a predetermined range.

42. The method of claim 38, wherein the cardiac signal is identified using a morphology of the separated signal, wherein the morphology satisfies a physiological characteristic.

43. The method of claim 35, further comprising forming an intermediate signal matrix by multiplying the composite signal matrix by a matrix composed of the eigenvectors corresponding to at least the two largest eigenvalues, and finding a unitary matrix corresponding to a rotational transformation of the intermediate signal matrix that increases the independence of the intermediate signals.

44. The method of claim 43, further comprising forming an independent signal matrix by multiplying the intermediate signal matrix by the unitary matrix, wherein the independent signal matrix comprises a set of independent signal vectors.

45. The method of claim 44, wherein a signal vector from the set of independent signal vectors is iteratively examined until a cardiac signal is identified.

46. The method of claim 45, wherein the cardiac signal is identified using a local peak density of the examined signal, wherein the local peak density is within a predetermined range.

47. The method of claim 45, wherein the cardiac signal is identified using beat detection on the examined signal, wherein a beat rate is within a predetermined range.

48. An implantable cardiac device, comprising:
a plurality of electrodes configured for subcutaneous non-intrathoracic sensing; and
a signal processor coupled to the plurality of electrodes, the signal processor configured to receive a composite signal associated with a plurality of sources sensed by at least two of the electrodes, and to extract a cardiac signal from the plurality of composite signals using blind source separation.

49. The device of claim 48, further comprising at least one lead coupled to the plurality of subcutaneous non-intrathoracic electrodes.

50. The device of claim 48, further comprising a plurality of leads coupled to the plurality of subcutaneous non-intrathoracic electrodes.

51. The device of claim 48, further comprising a plurality of leads, wherein at least one of the plurality of leads is coupled to an array of electrodes.

52. The device of claim 48, wherein the signal processor further comprises an adaptive filter, the adaptive filter altering its filtering characteristics based on a level of ambient noise.

53. The device of claim 52, wherein the level of ambient noise is determined using the independent component analysis.

54. The device of claim 48, wherein the blind source separation includes a principal component analysis that produces a set of eigenvalues and associated eigenvectors, and an eigenvector with a largest magnitude eigenvalue is used to extract the cardiac signal from the plurality of composite signals.

55. The device of claim 54, wherein a signal is separated iteratively from the plurality of composite signals using a next-largest magnitude eigenvalue for each iteration, until the cardiac signal is extracted from the plurality of composite signals.

56. An implantable cardiac device, comprising:
means for subcutaneously detecting a plurality of composite signals produced by a plurality of sources;
means for separating a signal from the plurality of composite signals "using blind source separation";and
means for identifying the separated signal as a cardiac signal.

57. The device of claim 56, wherein the separating means performs a principal component analysis on the plurality of composite signals.

58. The device of claim 56, wherein the separating means produces a set of eigenvalues and associated eigenvectors, and an eigenvector with a largest magnitude eigenvalue is used for separating the signal from the plurality of composite signals.

59. The device of claim 58, wherein the separating means iteratively separates the signal from the plurality of composite signals using a next-largest magnitude eigenvalue for each iteration, until the cardiac signal is separated from the plurality of composite signals.

60. The device of claim 56, further comprising means for detecting a cardiac condition using the cardiac signal.

61. The device of claim 60, further comprising means for treating the cardiac condition.

* * * * *

UNITED STATES PATENT AND TRADEMARK OFFICE
CERTIFICATE OF CORRECTION

| | | |
|---|---|---|
| PATENT NO. | : 7,236,819 B2 | Page 1 of 1 |
| APPLICATION NO. | : 10/741814 | |
| DATED | : June 26, 2007 | |
| INVENTOR(S) | : Marina Brockway | |

It is certified that error appears in the above-identified patent and that said Letters Patent is hereby corrected as shown below:

In the Claims

Claim 56, line 34: "signals "using blind source separation";" should be --signals using blind source separation;--.

Signed and Sealed this

Fourth Day of September, 2007

JON W. DUDAS
*Director of the United States Patent and Trademark Office*